US006615143B2

(12) United States Patent
Wu

(10) Patent No.: US 6,615,143 B2
(45) Date of Patent: Sep. 2, 2003

(54) METHOD AND APPARATUS FOR RECONSTRUCTING AND ACOUSTIC FIELD

(75) Inventor: Sean F. Wu, Troy, MI (US)

(73) Assignee: Wayne State University, Detroit, MI (US)

(*) Notice: Subject to any disclaimer, the term of this patent is extended or adjusted under 35 U.S.C. 154(b) by 147 days.

(21) Appl. No.: 09/796,862

(22) Filed: Mar. 1, 2001

(65) Prior Publication Data

US 2002/0165676 A1 Nov. 7, 2002

(51) Int. Cl.[7] ............................................... H04B 15/00
(52) U.S. Cl. ............................ 702/39; 702/138; 367/8; 367/129; 367/901
(58) Field of Search ........................ 702/39, 56; 367/1, 367/8, 13, 52, 129, 901; 73/587, 602, 646; 202/138

(56) References Cited

U.S. PATENT DOCUMENTS 5,712,805 A * 1/1998 Wang et al. .................. 367/1

OTHER PUBLICATIONS

Rasmussen, Spatial Transformation of Sound Fields, Sound and Vibration, May 1995.

Rasmussen, Tyre Noise Measurement on a Moving Vehicle, No Date.

* cited by examiner

*Primary Examiner*—Kamini Shah
(74) *Attorney, Agent, or Firm*—Carlson, Gaskey & Olds

(57) ABSTRACT

Acoustic field reconstruction is performed by expanding basis function which represent outgoing and incoming waves, without prior knowledge of the source geometry and dimensions. The reconstruction is based on acoustic pressures measured in the field only, and can be accomplished on a piece-wise basis. There are no restrictions on the locations of measurements. Moreover, the present invention can be used to reconstruct acoustic radiation from a plurality of sources or from a single source surrounded by multiple reflecting surfaces.

28 Claims, 2 Drawing Sheets

METHOD AND APPARATUS FOR RECONSTRUCTING AND ACOUSTIC FIELD

BACKGROUND OF THE INVENTION

The present invention provides rapid and accurate reconstruction of acoustic radiation from an arbitrarily shaped vibrating object.

Known methodologies deal with reconstructing acoustic radiation from a vibrating structure, also known as acoustic holography, which involves determining the vibration patterns on the surface of a structure based on simple acoustic pressure measurements from an array of microphones near the structure. A brief comparison of various methodologies that have been developed over the past two decades is given below.

The original nearfield acoustic holography (NAH) uses a plane wave expansion to represent the radiated acoustic field. The advantage of a planar NAH is that if the acoustic pressures over an infinite plane (called holography plane) can be measured continuously and exactly, the acoustic pressure and the normal component of the particle velocity anywhere including the source surface can be reconstructed with an infinite resolution. However, such a scenario can never be realized because in practice measurements are always discontinuous, measurement area is finite, and dynamic range of measurement devices is limited. Moreover, measurement and reconstruction are confined to a planar surface. Even so, this approach is not applicable when there are reflecting surfaces near the source or when the source is confined to interior space. These restrictions make the planar NAH suitable for reconstruction of acoustic radiation from a planar source, but not for an arbitrary surface in an exterior region.

To reconstruct acoustic radiation on the surface of an arbitrary object, one can utilize the Helmholtz integral theory that relates the field acoustic pressure to the acoustic quantities on the surface of the object. While this integral formulation is advantageous for a general surface, it has several inherent drawbacks.

The first drawback is the nonuniqueness of solutions to the surface Helmholtz integral equation. While this drawback can be overcome by the CHIEF method, there is no systematic way of determining the over-determined points in the interior region to yield a unique solution. The second drawback lies in the fact that the acoustic field is determined via a spatial discretization. In other words, the acoustic quantities are specified on certain discrete nodes and the measurements must be taken over a surface that completely encloses the source at once. For an arbitrary structure such as an engine vibrating in the low- to mid-frequency regime, the total number of discretized nodes on the surface can be very large, which necessitates taking a large number of measurements around the source. While one can use an iteration scheme to select the optimal measurement locations that may lead to more accurate reconstruction and that may reduce the overall number of measurement slightly, the process of this scheme itself can be very time-consuming. In any event, this approach requires the knowledge of source geometry and dimensions so as to generate a surface mesh. For an arbitrarily shaped structure, such a process can be very complex and time-consuming.

Another technique known as the HELS method is described in U.S. Pat. No. 5,712,805. In this method, the radiated acoustic pressure is expressed as an expansion of basis functions. The coefficients associated with these basis functions are determined by matching the assumed solution to the measured acoustic pressures. The errors incurred in this process are minimized by the least-squares method. Note that since the problem is often ill posed, it is critical to determine an optimal number of expansion functions, which depends on the signal to noise ratio (SNR), dynamic range of measurement devices, and standoff distances. The higher the SNR and dynamic range and the smaller the standoff distance, the larger the value of the optimum expansion number and the higher the accuracy of reconstruction.

The HELS method thus developed has been used to reconstruct acoustic radiation in both exterior and interior regions. One unique feature of this method is that it imposes no restrictions on the measurement locations. Moreover, the measurement aperture can be set comparable to the reconstruction area and reconstruction on the source surface can be carried out on a piecewise basis, which makes the whole process flexible and versatile.

It must be pointed out that the principle (i.e., expansion theory) underlying the HELS method has been discussed extensively in the past. For example, it has been used to analyze directivity patterns, far-field acoustic radiation based on nearfield measurements, sound radiation from a violin and antenna, noise source, and nearfield acoustic scanning.

An alternative to the spherical expansions is a collocation method first presented by Frazer, et al. as a means for satisfying differential equations at discrete points with a series expansion, which satisfies boundary conditions exactly. Alternatively, one can write the acoustic pressure in terms of a series expansion that satisfies the Helmholtz equation, whose coefficients are determined by requiring the solutions to satisfy the boundary conditions at certain discrete points in the least-squares sense. This finite-series expansion solution is discussed by Collatz and used by Meggs and Butler to predict far-field radiation based on the nearfield measurements.

Note that this boundary-collocation method is a variation of many related numerical techniques used to solve partial differential equations. These techniques are based on an assumed solution that satisfies the equation and/or boundary conditions exactly. The coefficients associated with this assumed solution can be determined using the least-squares, subdomain, collocation, or Galerkin's method, which are special cases of the general criterion that the weighted averages of the residual error must vanish. Each of these methods yields a different set of weighting functions.

All these techniques require the assumed solution to satisfy the boundary conditions at a number of points equal to that of the expansion coefficients. These unknown coefficients are then determined by taking a direct or pseudo-inversion of the resulting matrix equation. Such an approach works for prediction of far-field acoustic radiation that can be described effectively by a few expansion functions. However, it cannot be used to reconstruct the acoustic field on the source surface. This is because the inverse acoustic radiation problem is ill posed. Hence any slight error in the input data may be so magnified in the inversion of the matrix that the reconstructed acoustic field can be completely distorted.

Unlike the spherical expansion, the HELS formulation provides an approximate solution for the entire exterior region, with relatively higher accuracy of reconstruction outside the minimum sphere that encloses the source under consideration, and relatively lower accuracy inside. Moreover, one has complete freedom in selecting the measurement locations, can set a measurement aperture equal to the size of reconstruction, and carry out a piece-wise reconstruction over the source surface. This is in contrast with the Helmholtz integral theory based NAH, which requires taking measurements over a control surface that completely encloses the source. The size of the matrix equation of the HELS method is also much less than that of Helmholtz integral formulation, hence the former it is computationally more efficient than the latter. However, the accuracy of reconstruction provided by the HELS method can be poor for an irregularly shaped surface. This is because the number of basis functions necessary for reproducing the acoustic field on a rough surface may be significantly increased, while the presence of measurement errors keeps the number of expansion functions down, thus lowering the accuracy of reconstruction.

The above review indicates that none of the methodologies are perfect. The planar NAH is convenient for a planar source, but its use is very limited. The Helmholtz integral theory based NAH is advantages for an arbitrarily shaped surface, but is not practical. The HELS method is practical, but the accuracy of reconstruction is limited for a general source of smooth surface. In addition, all these methodologies suffer from a common failing; namely, they are not applicable when there are a plurality of sources or reflecting surfaces in the vicinity of the source under consideration.

SUMMARY OF THE INVENTION

The new algorithm used in the method and apparatus of the present invention is called "Complete Reconstruction of Acoustic Field Technology" or "CRAFT", which combines the advantages of the HELS method and the Helmholtz integral theory based NAH, but does not require a prior knowledge of the source geometry and dimensions. Accordingly, reconstruction can be done based on simple acoustic pressures measured in the field only, which significantly improves the numerical computation efficiency. Moreover, this algorithm can be used to reconstruct acoustic radiation from a plurality of sources or from a single source surrounded by multiple reflecting surfaces.

The input to the CRAFT algorithm is the field acoustic pressures measured around a vibrating object under consideration. No prior knowledge of the geometry and dimensions of the source are required. Once the formulation is established, the entire acoustic field that includes the surface and field acoustic pressures, normal component of the surface velocity, normal component of the time-averaged acoustic intensity, and acoustic energy flow is completely determined. Moreover, this algorithm allows for separation of the nearfield acoustic quantities from the farfield ones, thus enabling one to identify the components of surface vibrations that are responsible for sound radiation into the surrounding fluid medium.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENT

Figure 1:
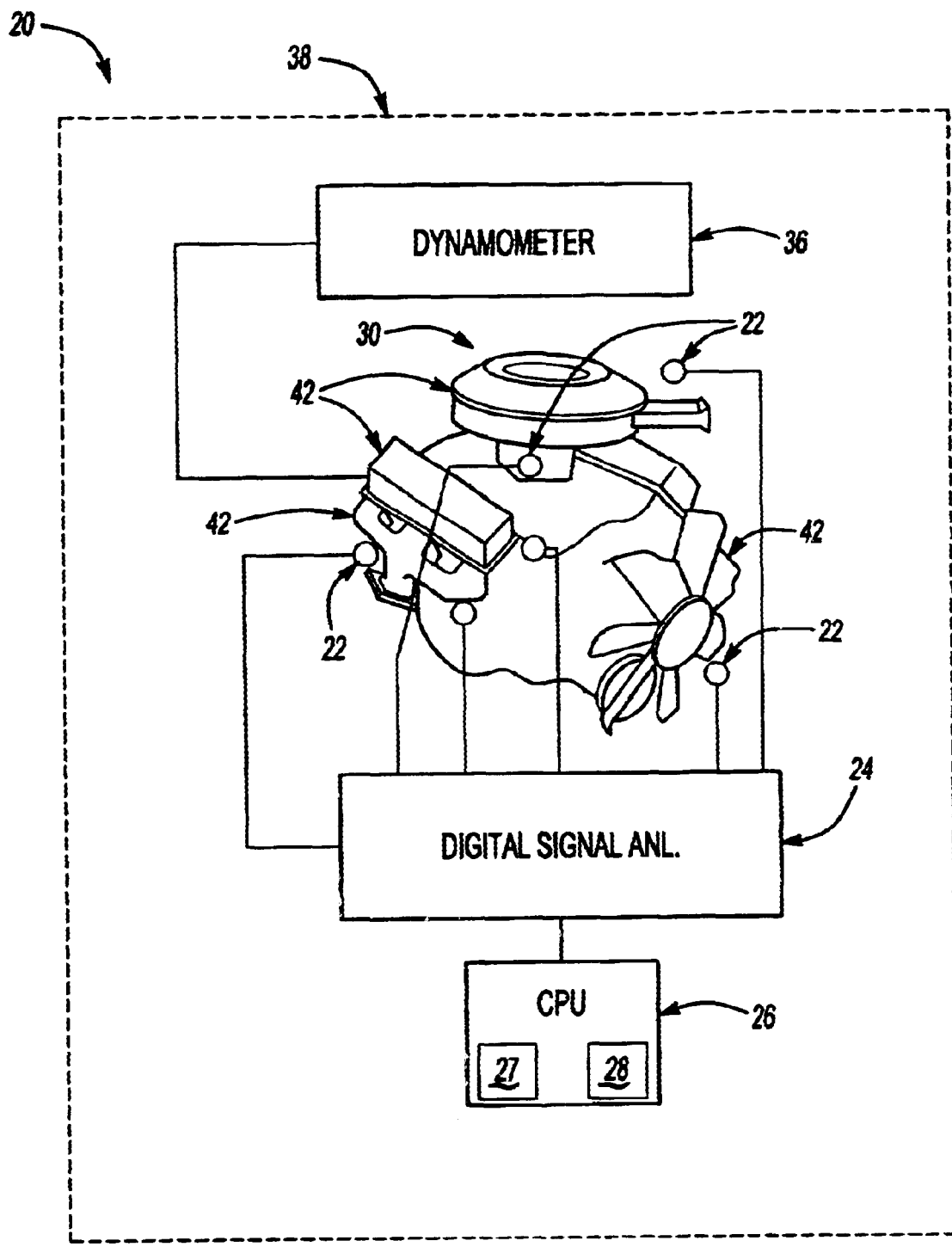
FIG. 1 is a schematic of the acoustic pressure reconstruction system of the present invention.

The acoustic pressure reconstruction system 20 of the present invention is shown schematically in FIG. 1. The system 20 generally comprises a plurality of transducers 22, or microphones, connected to a signal analyzer 24. Alternatively, a digital sound processing computer board or software algorithm could be used as signal analyzer 24. The system 20 further includes a computer 26 receiving and analyzing the data from the signal analyzer 24. As is well-known, the computer 26 includes a processor 27 operating a computer programs stored on computer-media 28, which may be one or more of RAM, ROM, hard-drive, CD-ROM, DVD, optical or magnetic media, or any other computer-readable medium. Computer media 28 includes a computer program, which when executed by processor 27 performs the steps described below, including performance of the CRAFT algorithm of the present invention.

The noise diagnostic system 20 can be used to diagnose noise sources and quantify their strengths in order to facilitate efforts to reduce noise levels. For illustrative purposes only, and not by way of limitation, the present invention will be shown and described for use in diagnosing the sources of noise from automobile engine 30.

The automobile engine 30 is preferably connected to a dynamometer 36 inside an anechoic chamber 38. In FIG. 1, six transducers 22 are placed adjacent to the engine components 42 inside the anechoic chamber 38. The number of transducers 22 used depends upon the complexity of the shape of the object and the accuracy desired, but at least two transducers 22 are required.

Generally, in operation, the transducers 22 measure the frequency and amplitude of noise while the engine 30 is running. The gathered data is sent to the signal analyzer 24 which indicates amplitude as a function of frequency. This frequency/amplitude data is sent to the computer 26. The computer 26 determines the amplitudes of each frequency caused by each engine component 42 by, reconstructing the acoustic field on the surface of the components 42 based upon the frequency/amplitude data from the signal analyzer 24. The computer 26 utilizes an inventive method which will be referred to here as the "Complete Reconstruction of Acoustic Field Technology", or "CRAFT" Method, more fully explained below, to obtain the noise source distribution. This noise source distribution facilitates the reduction of noise by identifying the components 42 which are generating certain amplitudes and frequencies. The CRAFT algorithm will first be described below, followed by a description with respect to FIG. 2 of the use of the CRAFT algorithm by the system of FIG. 1.

In the CRAFT algorithm the radiated acoustic pressure is assumed to be expressible as $$\hat{p}(\vec{x},\omega) = \{\Psi\}_{J\times 1}^{T}\{C\}_{J\times 1} + \{\Psi^*\}_{J\times 1}^{T}\{D\}_{J\times 1} \tag{1}$$

where $\hat{p}(\vec{x},\omega)$ represents the complex amplitude of acoustic pressure at a field point $\vec{x}$, and $\{\Psi\}$ represents a set of basis functions with a superscript $\{\Psi^*\}$ implying its complex conjugate. Physically, the two terms on the right side of Eq. (1) represent the effects of out-going and incoming spherical waves, respectively. The basis functions $\{\Psi\}$ can be written in the spherical coordinates as $$\Psi_j(r,\theta,\phi) = [j_n(kr) + iy_n(kr)]Y_n^m(\theta,\phi), \tag{2}$$

where $j_n(kr)$ and $y_n(kr)$ represent the spherical Bessel functions of the first and second kinds, respectively, and $Y_n^m(\theta,\phi)$ are the spherical harmonics defined by $$Y_n^m(\theta, \phi) = \sqrt{\frac{(2n+1)}{4\pi} \frac{(n-m)!}{(n+m)!}} P_n^m(\cos\theta) e^{im\phi}, \quad (3)$$

where $P_n^m(\cos\theta)$ are the associated Legendre functions of the first kind, which is identically zero when m>n. The relation between the indices j, n, and m in Eq. (2) are shown in Table 1.

TABLE 1

Relationship among indices j, n, and m.

| j | n | m |
|---|---|---|
| 1 | 0 | 0 |
| 2 | 1 | 0 |
| 3 | 1 | −1 |
| 4 | 1 | 1 |
| 5 | 2 | 0 |
| 6 | 2 | −1 |
| 7 | 2 | 1 |
| 8 | 2 | −2 |
| 9 | 2 | 2 |

The coefficients $\{C\}_{J\times 1}$ and $\{D\}_{J\times 1}$ in Eq. (1) are determined by matching the assumed solution to the measured pressures.

$$\{\hat{p}(\vec{x}_m, \omega)\}_{M\times 1} = [\Psi]_{M\times J}\{C\}_{J\times 1} + [\Psi^*]_{M\times J}\{D\}_{J\times 1}, \quad (4)$$

where $\vec{x}_m$ indicates a measurement loccation, m=1 to M. If J expansion functions in Eq. (1) are used, then M measurements must be taken, where M≧2J. To minimize the errors incurred in this process, the least-squares method is used, which results in the following two equations $$[\Psi]_{M\times J}^T[\Psi]_{M\times J}\{C\}_{J\times 1} + [\Psi]_{M\times J}^T[\Psi^*]_{M\times J}\{D\}_{J\times 1} = [\Psi]_{M\times J}^T\{\hat{p}(\vec{x}_m, \omega)\}_{M\times 1}, \quad (5a)$$

$$[\Psi^*]_{M\times J}^T[\Psi]_{M\times J}\{C\}_{J\times 1} + [\Psi^*]_{M\times J}^T[\Psi^*]_{M\times J}\{D\}_{J\times 1} = [\Psi^*]_{M\times J}^T\{\hat{p}(\vec{x}_m, \omega)\}_{M\times 1}, \quad (5b)$$

where the superscript T indicates a transposition of the matrix. The coefficients $\{C\}_{J\times 1}$ and $\{D\}_{J\times 1}$ in Eq. (5) can be obtained by taking a pseudo-inverse $$\{C\}_{J\times 1} = \{[E_{11}]_{J\times M} - [E_{12}]_{J\times J}([I]_{J\times J} - [E_{21}]_{J\times J}[E_{12}]_{J\times J})^{-1}([E_{22}]_{J\times M} - [E_{21}]_{J\times J}[E_{11}]_{J\times M})\}\{\hat{p}(\vec{x}_m, \omega)\}_{M\times 1}$$

$$\{D\}_{J\times 1} = ([I]_{J\times J} - [E_{21}]_{J\times J}[E_{12}]_{J\times J})^{-1}([E_{22}]_{J\times M} - [E_{21}]_{J\times J}[E_{11}]_{J\times M})\{\hat{p}(\vec{x}_m, \omega)\}_{M\times 1}, \quad (6)$$

where $[I]_{J\times J}$ represents an identity matrix and $[E_{11}]_{J\times M}$, $[E_{12}]_{J\times J}$, $[E_{21}]_{J\times J}$, and $[E_{22}]_{J\times M}$ are the transfer matrices defined by $$[E_{11}]_{J\times M} = ([\Psi]_{M\times J}^T[\Psi]_{M\times J})^{-1}[\Psi]_{M\times J}^T, \quad (7a)$$

$$[E_{12}]_{J\times J} = ([\Psi]_{M\times J}^T[\Psi]_{M\times J})^{-1}[\Psi]_{M\times J}^T[\Psi^*]_{M\times J}, \quad (7b)$$

$$[E_{21}]_{J\times J} = ([\Psi^*]_{M\times J}^T[\Psi^*]_{M\times J})^{-1}[\Psi^*]_{M\times J}^T[\Psi]_{M\times J}, \quad (7c)$$

$$[E_{22}]_{J\times M} = ([\Psi^*]_{M\times J}^T[\Psi^*]_{M\times J})^{-1}[\Psi^*]_{M\times J}^T. \quad (7d)$$

Note that the least-squares method always gives the best fit of the assumed solution to the measured data. Hence the accuracy in reconstruction at measurement locations increases monotonically with the number of expansion functions in Eq. (4). On the other hand, the accuracy in reconstruction on the source surface increases with the number of expansion functions at first, and then deteriorates thereafter due to an inherent ill-conditioning difficulty. Therefore, it is imperative to find an optimal number $J_{op}$, which can be accomplished either by minimizing the sum of $\|L\|^2$ errors in reconstruction through an iteration scheme or using a constrained minimization through a quadratic programming technique.

Once the optimal number of expansion coefficients $\{C\}_{J_{op}\times 1}$ and $\{D\}_{J_{op}\times 1}$ are determined, the acoustic field throughout the entire exterior region including the source surface is completely determined. Having obtained the surface acoustic pressure, the complex amplitude of the normal component of the surface velocity $\hat{v}_n(\vec{x}_S, \omega)$ can be determined by the Euler's equation $$\hat{v}_n(\vec{x}_S, \omega) = \frac{1}{i\omega\rho_0}\left(\left\{\frac{\partial\Psi}{\partial n}\right\}_{J_{op}\times 1}^T\{C\}_{J_{op}\times 1} + \left\{\frac{\partial\Psi^*}{\partial n}\right\}_{J_{op}\times 1}^T\{D\}_{J_{op}\times 1}\right), \quad (8)$$

where $\rho_0$ is the fluid density and $\partial/\partial n$ represents a normal derivative.

Once the surface acoustic pressure and the normal component of the surface velocity are specified, the time-averaged acoustic intensity can be calculated by $$I_{n,av}(\vec{x}_S, \omega) = \frac{1}{2}\text{Re}[\hat{p}(\vec{x}_S, \omega)\hat{v}_n^*(\vec{x}_S, \omega)]. \quad (9)$$

Equation (9) enables one to visualize the acoustic energy flow from the surface of a vibrating object into the surrounding fluid medium. This three-dimensional image of acoustic radiation together with the normal component of surface velocity field can be very helpful in providing a better understanding of correlation between structural vibrations and sound radiation. In particular, one can take the leading order terms as kr→∞ in the basis functions $\{\Psi\}^{super}$ to derive asymptotic solutions for the supersonic components of the surface velocity $\hat{v}_n^{super}(\vec{x}_S, \omega)$ and time-averaged acoustic intensity $I_{n,av}^{super}(\vec{x}, \omega)$ $$I_{n,av}^{super}(\vec{x}_S, \omega) = \frac{1}{2}\text{Re}[\hat{p}^{super}(\vec{x}_S, \omega)\hat{v}_n^{super*}(\vec{x}_S, \omega)]. \quad (10)$$

Note that Eqs. (8) and (9) represent the total normal components of the surface velocity and the time-averaged acoustic intensity, respectively. Whereas Eq. (10) gives the supersonic components of the surface velocity and time-averaged acoustic intensity, which are responsible for acoustic radiation to the farfield. Therefore, the information acquired from Eqs. (8) to (10) enables one to relate the components of surface vibration to acoustic radiation to the farfield.

Figure 2:
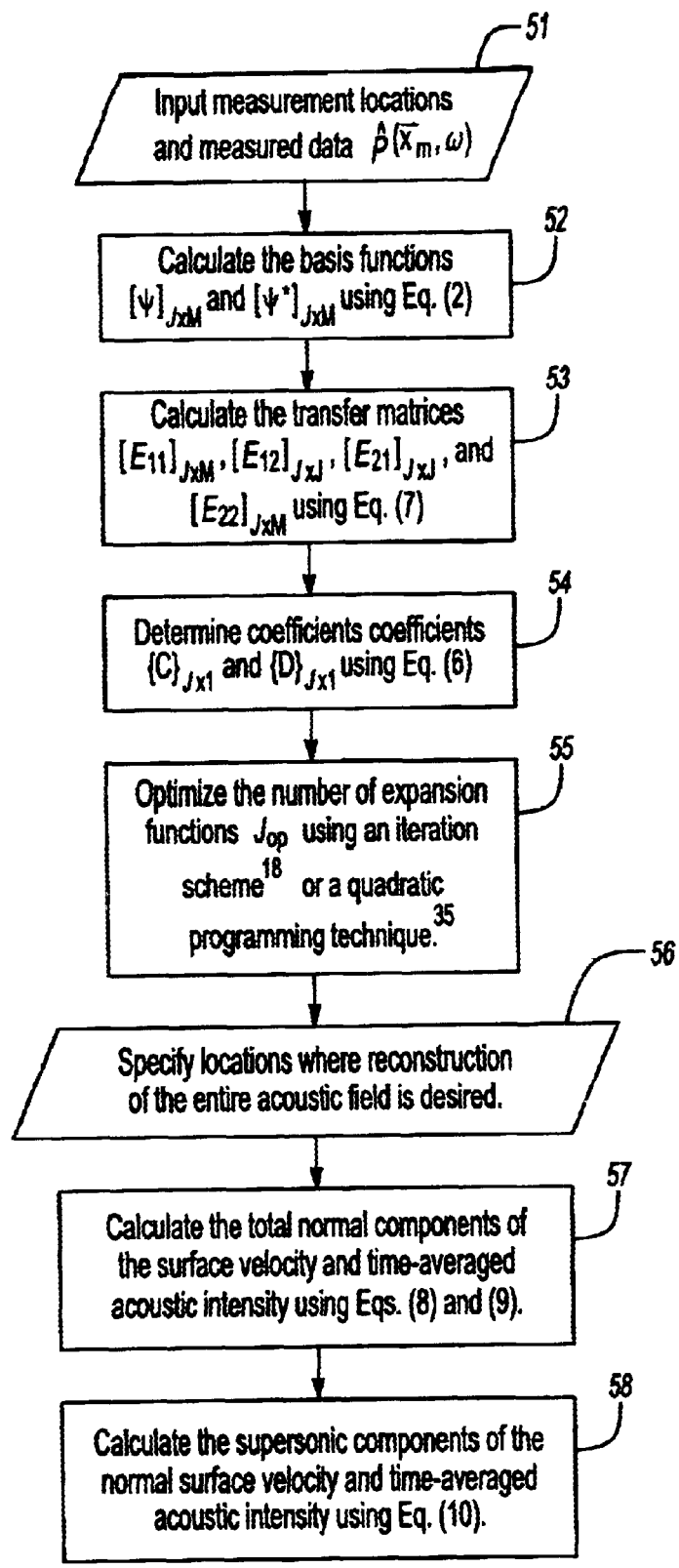
FIG. 2 is a flowchart illustrating the operation of the system of FIG. 1.

FIG. 2 illustrates the method of the present invention in implementing the CRAFT algorithm as performed by the system of FIG. 1. In step 51 of FIG. 2, measurement data from the transducers 22 (and signal analyzer 24—FIG. 1) and the measurement locations are input to the CPU 26. In step 52, the basis functions are calculated by CPU 26 using Eq. (2), above, of the CRAFT algorithm. In step 53, the CPU 26 calculates the transfer matrices using Eq. (7). The coefficients $\{C\}_{J\times 1}$ and $\{D\}_{J\times 1}$ in Eq. (1) are determined in step 54 using Eq. (6). In step 55, the number of expansion functions is optimized by CPU 26.

At this point, the acoustic field can be determined at any point without reference to the geometry of the noise source, in this example, components 42. In step 56, the locations where reconstruction of the entire acoustic field is desired is specified by a user or other input to the CPU 26. The CPU 26 then calculates the total normal components of the surface velocity and time-averaged acoustic intensity using Eq. (8) and (9) in step 57. The CPU 26 also calculates the supersonic components of the normal surface velocity and time-averaged acoustic intensity using Eq. (10) in step 58.

The CRAFT algorithm of the present invention is superior to all the current NAH technologies in several ways. It does not require a prior knowledge of the geometry and dimensions of the source under consideration, which is in contrast with both the HELS method and the Helmholtz integral theory based NAH. This feature makes the CRAFT algorithm extremely efficient in numerical computations.

The only input to the CRAFT algorithm is the acoustic pressures measured at a plurality of points surrounding the source under consideration. There is no restriction on where the measurement should be taken. This makes the CRAFT algorithm versatile in practice.

The effect of out-going and in-coming spherical waves is accounted for in the CRAFT algorithm as indicated in Eq. (1). This salient feature not only allows the CRAFT algorithm to yield highly accurate reconstruction of acoustic radiation from an arbitrarily shaped object, but also enables it to be used in situations where there are a plurality of sources or when the source under consideration is surrounded by multiple reflecting surfaces.

Once the coefficients $\{C\}_{J_{op} \times 1}$ and $\{D\}_{J_{op} \times 1}$ are obtained, where $J_{op}$ implies an optimal number of expansion functions, the acoustic field anywhere including the source surface is completely determined.

The output of the CRAFT algorithm includes the acoustic pressures, normal component of surface velocity, and normal component of time-averaged acoustic intensity.

In addition, the CRAFT algorithm can provide the supersonic components of the surface velocity and time-averaged acoustic intensity. The combination of items 5 and 6 enables one to identify the specific component of surface vibration that is responsible for acoustic radiation to the farfield, which can be very helpful to engineers in diagnosing noise and vibrations of a complex machine in the manufacturing industry.

The CRAFT algorithm is applicable to both exterior and interior regions. The CRAFT algorithm allows for piecewise reconstruction of acoustic radiation, which makes it very practical and versatile in engineering applications.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A method for reconstructing acoustic radiation from a noise source of unknown geometry including the steps of:
   a) measuring sound at a plurality of measurement points in a field around the noise source of unknown geometry, the field having at least one reflective surface; and
   b) reconstructing the acoustic field at points other than the measurement points.

2. The method of claim 1 wherein said step b) is performed without reference to the geometry of the noise source.

3. A method for reconstructing acoustic radiation from a noise source of unknown geometry including the steps of:
   a) measuring sound at a plurality of measurement points around the noise source of unknown geometry;
   b) reconstructing the acoustic field at points other than the measurement points; and
   c) using outgoing and incoming waves to approximate the acoustic radiation from the noise source of unknown geometry.

4. The method of claim 1 further including the step of providing the supersonic components of the surface velocity and time-averaged acoustic intensity.

5. The method of claim 1 further including the step of assuming the radiated acoustic pressure as outgoing waves and incoming waves.

6. The method of claim 5 further including the step of expanding basis functions which represent the outgoing waves and the incoming waves.

7. A method for reconstructing acoustic radiation from a noise source including the steps of:
   a) measuring sound at a plurality of measurement points around the noise source in a field having at least one reflective surface; and
   b) reconstructing the acoustic field at points other than the measurement points without reference to a geometry of the noise source.

8. The method of claim 7 further including the step of assuming the radiated acoustic pressure as a superposition of effects of outgoing waves and incoming waves.

9. The method of claim 8 further including the step of expanding basis functions that represent the outgoing waves and the incoming waves.

10. The method of claim 7 wherein said step a) includes the step of determining a complex amplitude of acoustic pressure.

11. The method of claim 7 wherein said step b) further includes the step of:
    c) calculating an outgoing wave basis function which represents outgoing waves and an incoming wave basis function which represents incoming waves.

12. The method of claim 11 wherein said step b) further includes the step of:
    d) determining a coefficient of the outgoing wave basis function; and
    e) determining a coefficient of the incoming wave basis function.

13. The method of claim 12 wherein said step b) further includes the step of:
    f) optimizing the number of expansion functions.

14. The method of claim 12 wherein said step b) further includes the step of:
    f) specifying a location; and
    g) reconstructing field and surface acoustic pressures, normal components of surface velocity and time-averaged acoustic intensity at the specified location.

15. The method of claim 14 wherein said step b) further includes the step of:
    h) reconstructing supersonic components of surface acoustic pressure, normal components of surface velocity and time-averaged acoustic intensity at the specified location.

16. A system for reconstructing an acoustic field comprising:
    a plurality of transducers each for measuring acoustic pressure at a measurement point around a noise source;
    a computer reconstructing the acoustic field at points other than the measurement points without reference to a geometry of the noise source based upon the acoustic pressure as measured by said transducers and by using outgoing and incoming waves to approximate acoustic radiation from the noise source of unknown geometry.

17. The system of claim 16 wherein the computer provides the supersonic components of the surface velocity and time-averaged acoustic intensity.

18. The system of claim 16 wherein the computer assumes the radiated acoustic pressure as outgoing waves and incoming waves.

19. A computer-readable storage medium used to direct a computer for reconstructing an acoustic field to perform the functions of:
   a) receiving measurements of sound at a plurality of measurement points in a field around a noise source of unknown geometry, the field having at least one reflective surface; and
   b) reconstructing the acoustic field at points other than the measurement points.

20. The medium of claim 19 wherein said step b) is performed without reference to the geometry of the noise source.

21. The medium of claim 19 further including the step of assuming the radiated acoustic pressure as a superposition of effects of outgoing waves and incoming waves.

22. The medium of claim 21 further including the step of expanding basis functions that represent the outgoing waves and the incoming waves.

23. The medium of claim 22 wherein said step a) includes the step of determining a complex amplitude of acoustic pressure.

24. The medium of claim 23 wherein said step b) further includes the step of:
   c) calculating an outgoing wave basis function which represents outgoing waves and an incoming wave basis function which represents incoming waves.

25. The medium of claim 23 wherein said step b) further includes the step of:
   d) determining a coefficient of the outgoing wave basis function; and
   e) determining a coefficient of the incoming wave basis function.

26. The medium of claim 25 wherein said step b) further includes the step of:
   f) optimizing the number of expansion functions.

27. The medium of claim 12 wherein said step b) further includes the step of:
   g) specifying a location; and
   h) reconstructing field and surface acoustic pressures, normal components of surface velocity and time-averaged acoustic intensity at the specified location.

28. The medium of claim 27 wherein said step b) further includes the step of:
   i) reconstructing supersonic components of surface acoustic pressure, normal components of surface velocity and time-averaged acoustic intensity at the specified location.

* * * * *

UNITED STATES PATENT AND TRADEMARK OFFICE
CERTIFICATE OF CORRECTION

PATENT NO. : 6,615,143 B2
DATED : September 2, 2003
INVENTOR(S) : Sean F. Wu

It is certified that error appears in the above-identified patent and that said Letters Patent is hereby corrected as shown below:

<u>Title page,</u>
Item [54], Title, should read as follows:
-- METHOD AND APPARATUS FOR RECONSTRUCTING AN ACOUSTIC FIELD --

Signed and Sealed this

Eighteenth Day of May, 2004

JON W. DUDAS
*Acting Director of the United States Patent and Trademark Office*